United States Patent [19]

Van Tuttle et al.

[11] Patent Number: 5,574,149
[45] Date of Patent: *Nov. 12, 1996

[54] METHOD OF TREATING HIV INFECTIONS WITH 2',3'-DIDEOXY-3'-FLUORO-5-CHLOROURIDINE

[75] Inventors: Joel Van Tuttle, Durham; Susan M. Daluge, Chapel Hill; Charlene L. Burns, Durham; George W. Koszalka; Thomas A. Krenitsky, both of Chapel Hill, all of N.C.

[73] Assignee: Glaxo Wellcome Inc., Research Triangle Park, N.C.

[*] Notice: The portion of the term of this patent subsequent to Oct. 16, 2007, has been disclaimed.

[21] Appl. No.: 62,591

[22] Filed: May 17, 1993

Related U.S. Application Data

[63] Continuation of Ser. No. 709,083, May 30, 1991, abandoned, which is a continuation of Ser. No. 267,244, Nov. 4, 1988, abandoned.

[30] Foreign Application Priority Data

Nov. 7, 1987 [GB] United Kingdom .................. 8762136

[51] Int. Cl.$^6$ ......................... A61K 31/70; C07H 19/073
[52] U.S. Cl. ............................................. 536/50; 536/28.55
[58] Field of Search .......................... 514/50; 536/28.55, 536/28.2

[56] References Cited

U.S. PATENT DOCUMENTS 3,328,388  6/1967  Shen et al. ........................... 536/28.52
5,153,180  10/1992  Mattes et al. ............................ 514/50

FOREIGN PATENT DOCUMENTS

WO88/00050  1/1988  WIPO .

OTHER PUBLICATIONS

Matthes et al., "3'-Fluoro-substituted Deoxynucleosides As Potential Anti-AIDS Drugs", paper presented at symposium on AIDS, Berlin, Sep. 7-10, 1988.

Jan Balzarini, et al.; 5-Halogeno-3'-fluoro-2', 3'-dideoxyuridines as Inhibitors of Human Immunodeficiency Virus (HIV); Potent and Selective Anti-HIV Acitivity of 3'-Fluoro-2',3'-dideoxy-5-chlorouridine; 1989; pp. 571-577.

Susan Daluge et al.; 5-Chloro-2', 3-Dideoxy-3'Fluorouridine (935U83), a Selective Anti-Human Immunodeficiency Virus Agent with and Improved Metabolic and Toxicological Profile; Vo. 38; No. 7; May 9, 1994; pp. 1590-1603.

*Primary Examiner*—Gary L. Kunz
*Attorney, Agent, or Firm*—Karen L. Prus

[57] ABSTRACT

A method for treating HIV infections comprising administering a composition whose active ingredient is 2',3'-dideoxy-3'-fluoro-5'-chlorouridine.

8 Claims, No Drawings

METHOD OF TREATING HIV INFECTIONS WITH 2',3'-DIDEOXY-3'-FLUORO-5-CHLOROURIDINE

This is a continuation of application Ser. No. 07/709,083 filed on May 30, 1991, now abandoned, which is a continuation of Ser. No. 07/267,244 filed Nov. 4, 1988 now abandoned.

The present invention relates to certain 3'-fluoro-2',3'-dideoxynucleosides, pharmaceutically acceptable derivatives thereof, and their use in therapy, particularly for the treatment of certain viral infections.

In the field of antiviral chemotherapy, few drugs exist which effectively combat the virus per se, owing to the difficulty of attacking the virus while leaving uninfected host cells unimpaired. It has recently been established that certain stages in the virus life-cycle, which vary from species to species, are specified by the virus itself. These stages may prove susceptible to attack where they differ sufficiently from any corresponding host-cell function. However, owing to great similarity between viral and host functions, effective treatments have proven very difficult to identify.

One group of viruses which has recently assumed a particular importance are the retroviruses. Retroviruses form a sub-group of RNA viruses which, in order to replicate, must first 'reverse transcribe' the RNA of their genome into DNA ('transcription' conventionally describes the synthesis of RNA from DNA). Once in the form of DNA, the viral genome is incorporated into the host cell genome, allowing it to take full advantage of the host cell's transcription/translation machinery for the purposes of replication. Once incorporated, the viral DNA is virtually indistinguishable from the host's DNA and, and in this state, the virus may persist for as long as the cell lives. As it is believed to be invulnerable to attack in this form, any treatment must be directed at another stage of the virus life cycle and would, have to be continued until all virus-infected cells have died.

A species of retrovirus has also been reproducibly isolated from patients with AIDS and is now named as human immunodeficiency virus (HIV) and is also know as human T-cell lymphotropic virus III (HTLV III), AIDS associated retrovirus (ARV), or lymphadanopathy associated virus (LAV). This virus has been shown preferentially to infect and destroy T-cells bearing the $OKT^4$ surface marker and is now generally accepted as the aetiologic agent of AIDS. The patent progressively loses this set of T-cells, upsetting the overall balance of the immune system, reducing his ability to combat other infections, and predisposing him to opportunistic infections which frequently prove fatal. Thus, the usual cause of death in AIDS victims is by opportunistic infection, such as pneumonia or virally induced cancers, and not as a direct result of HIV infection.

Recently, HIV has also been recovered from other tissue types, including B-cells expressing the $T^4$ marker, macrophages and non-blood associated tissue in the central nervous system. This infection of the central nervous system has been discovered in patients expressing classical AIDS symptoms and is associated with progressive demyelination, leading to wasting and such symptoms as encephalopathy, progressive dysarthria, ataxia and disorientation. Further conditions associated with HIV infection are the asymptomatic carrier state, progressive generalised lymphadenopathy (PGL) and AIDS-related complex (ARC).

We have now discovered that certain 3'-fluoro-2',3'-dideoxynucleosides, as referred to below, are useful for the treatment of viral infections, particularly retroviral infections and especially HIV infections such as AIDS, ARC, PGL and carriers of HIV.

Preferably the 3'-fluoro-2',3'-dideoxynucleosides of the present invention have the following formula (I):

wherein B represents a group of formula

or

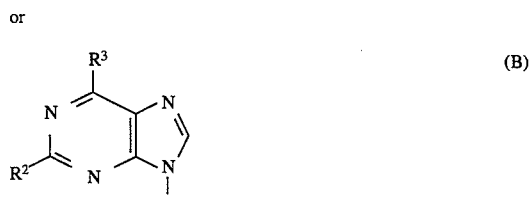

in which $R^1$ represents a hydrogen, chlorine or iodine atom, $R^2$ represents an amino group and $R^3$ represents a $C_{3-6}$ cycloalkylamino (e.g. cyclopropylamino), $C_{1-6}$ straight or branched chain alkoxy (e.g. methoxy), $C_{3-7}$ cycloalkoxy (e.g. cyclopentoxy) or a 5- or 6-membered heterocyclic ring bonded to the purine residue via a nitrogen atom in the said ring (e.g. piperidinyl) or a pharmaceutically acceptable derivative thereof, for use in the treatment of a viral infection. The above compounds of formula (I) and their pharmaceutically acceptable derivatives are hereinafter referred to as the compounds according to the invention.

Other useful compounds according to the present invention include compounds of formula (I) wherein $R^2$ represents a hydrogen atom.

The compounds according to the invention have particularly good activity against human retroviruses for example human T-cell Lymphotropic viruses (HTLV), especially HTLV-I, HTLV-II and HIV (HTLV-III); The invention accordingly provides the compounds according to the invention for use in the treatment of prophylaxis of any of the above infections. The present invention also provides, as novel compounds, the compounds of formula (I) in which B represents a group of formula (B) above and their pharmaceutically acceptable derivatives.

The compounds according to the invention are also useful for the treatment of other clinical conditions associated with retroviral infections, for example, Kaposi's sarcoma, thrombocytopenic purpura, AIDS-related complex, and patients carrying AIDS-antibodies or who are seropositive to the AIDS virus, as well as chronic neurological conditions such as multiple sclerosis or tropical spastic paraparesis. The compounds according to the invention are also useful for the treatment of HTLV-I, HTLV-II, HTLV-IV and HIV-2 infections as well as other human retrovirus infections associated with AIDS or immunodeficiency, and also psoriasis. The invention accordingly provides the compounds according to the invention for use in the treatment of any of the above infections or conditions.

Particularly good activity has been observed against those viruses which are retroviruses and also those DNA viruses which, like retroviruses, are incorporated into the host genome during their life-cycle, i.e. retrovirus-like DNA viruses. Thus, there is further provided the compounds according to the invention for use in the treatment of retroviral, or retrovirus-like infections.

It will be appreciated that the compounds according to the invention may also be used in the manufacture of a medicament for the treatment of any of the above-mentioned medical or veterinary indications.

By "a pharmaceutically acceptable derivative" is meant any pharmaceutically acceptable salt, 5'-ester, 5'-secondary the (e.g. isopropyl ether) or salt of such ester or ether of a compound of formula (I), or any other compound, which, upon administration to the recipient, is capable of providing (directly or indirectly) such a compound or an antivirally active metabolic or residue thereof.

Preferred esters of the compounds of formula (I) include carboxylic acid esters in which the non-carbonyl moiety of the ester grouping is selected from straight or branched chain alkyl, alkoxyalkyl (e.g. methoxymethyl), aralkyl (e.g. benzyl), aryloxyalkyl (e.g. phenoxymethyl), aryl (e.g. phenyl optionally substituted by halogen $C_{1-4}$ alkyl or $C_{1-4}$ alkoxy); sulphonate esters such as alkyl- or aralkylsulphonyl (e.g. methanesulphonyl); amino acid esters; and mono-, di- or tri-phosphate esters.

With regard to the above-mentioned esters, unless otherwise specified, any alkyl moiety present advantageously contains 1 to 18 carbon atoms, particularly 1 to 5 carbon atoms. Any aryl moiety present in such esters advantageously comprises a phenyl group.

Any reference to any of the above compounds also includes a reference to a pharmaceutically acceptable salt thereof.

Examples of pharmaceutically acceptable salts of the compounds of formula (I) and pharmaceutically acceptable derivatives thereof include base salts, eg derived from an appropriate base, such as alkali metal (e.g. sodium), alkaline earth metal (e.g. magnesium) salts, ammonium and $NX_4^+$ (wherein X is $C_{1-4}$ alkyl). Physiologically acceptable salts of any hydrogen atom or an amino group include salts of organic carboxylic acids such as acetic, lactic, tartaric, malic, isethionic, lactobionic and succinic acids; organic sulfonic acids such as methanesulfonic, ethanesulfonic, benzenesulfonic and p-tolunesulfonic acids and inorganic acids such as hydrochloric, sulfuric, phosphoric and sulfamic acids. Physiologically acceptable salts of a compound of any hydroxy group include the anion of said compound in combination with a suitable cation such as $Na^+$, $NH_4^+$, and $NX_4^+$ (wherein X is a $C_{1-4}$ alkyl group).

Preferred compound of formula (I) include these in which $R^2$ represents an amino group and $R^3$ represents a $C_{1-6}$ alkoxy group.

Examples of compounds of formula (I) above include:

1. 2',3'-dideoxy-3'-fluorouridine
2. 5-iodo-1-(2,3-dideoxy-3-fluoro-β-D-erythro-pentofuranosyl)uracil
3. 5-chloro-1-(2,3-dideoxy-3-fluoro-β-D-erythro-pentofuranosyl)uracil
4. 6-cyclopropylamino-9-(β-D-2,3-dideoxy-3-fluororibofuranosyl)-9H-purine
5. 2-amino-6-methoxy-9-(β-D-2,3-dideoxy-3-fluororibofuranosyl)-9H-purine
6. 6-cyclopentoxy-9-(β-D-2,3-dideoxy-3-fluororibofuranosyl)-9H-purine
7. 6-isopropoxy-9-(β-D-2,3-dideoxy-3-fluororibofuranosyl)-9H-purine
8. 6-piperidinyl-9-(β-D-2,3-dideoxy-3-fluororibofuranosyl)-9H-purine The compounds according to the invention, also referred to herein as the active ingredient, may be administered for therapy by any suitable route including oral, rectal, nasal, topical (including buccal and sublingual), vaginal and parenteral (including subcutaneous, intramuscular, intravenous and intradermal). It will be appreciated that the preferred route will vary with the condition and age of the recipient, the nature of the infection and the chosen ingredient.

In general a suitable dose will be in the range of 0.1 to 120 mg per kilogram body weight of the recipient per day, preferably in the range of 0.5 to 40 mg per kilogram body weight per day and most preferably in the range 1 to 15 mg per kilogram body weight per day. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Ideally, the active ingredient should be administered to achieve peak plasma concentrations of the active compound of from about 1 to about 75 µm preferably about 2 to 50 µm, most preferably about 3 to about 30 µm. This may be achieved, for example, by the intravenous injection of a 0.1 to 5% solution of the active ingredient, optionally in saline, or orally administered as a bolus containing about 1 to about 100 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to the administered alone it is preferable to present it as a pharmaceutical formulation. The formulations of the present invention comprise at least one active ingredient, as above defined, together with one or more acceptable carriers therefor and optionally other therapeutic agents. Each carrier must be "acceptable" in the sense of being compatible with the other ingredients of the formulation and not injurious to the patient. Formulations include those suitable for oral, rectal, nasal, topical (including buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution of a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach. This is particularly advantageous where, in the compounds of formula (I), B is a purine, as such compounds are susceptible to acid hydrolysis.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

The above compounds of the present invention and their pharmaceutically acceptable derivatives may be employed in combination with other therapeutic agents for the treatment of the above infections or conditions. Examples of such further therapeutic agents include agents that are effective for the treatment of HIV infections or associated conditions, such as 3'-azido-3'-deoxythymidine (zidovudine), compounds that complement, enhance or potentiate the activity of the compounds according to the invention such as 2',3'-dideoxynucleosides such as 2',3'-dideoxy-cycidine, -adenosine or -inosine, carbocyclic nucleoside analogues such as carbovir, acyclic nucleosides (eg acyclovir), interferons such as α-interferon, renal excretion inhibitors such as probenecid or nucleoside transport inhibitors such as dipyridamole, as well as immunomodulators such as interleukin II and granulocyte macrophage colony stimulating factors.

It should be understood that in addition to the ingredients particularly mentioned above the formulations of this invention may include other agents conventional in the art having regard to the type of formulation in question, for example, those suitable for oral administration may include such further agents as sweeteners, thickeners and flavouring agents.

The present invention further includes a process for the preparation of a compound of formula (I) and pharmaceutically acceptable derivatives thereof which comprises either:

(A) reacting a compound of formula:

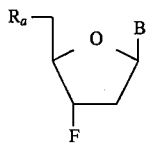

(II)

wherein B is as hereinbefore defined, and $R_a$ represents a precursor group for the hydroxy group, or for a pharmaceutically acceptable derivative group thereof, with an agent or under conditions serving to convert the said precursor group into the corresponding desired group; or (B) reacting a purine or pyrimidine base of formula $$B-H \qquad \text{III}$$

(wherein B is as hereinbefore defined).

or a functional equivalent thereof, with a compound serving to introduce the desired ribofuranosyl ring at the 9- or 1-position respectively of the purine or pyrimidine base of formula (III):
and thereafter, or simultaneously therewith, effecting one or more of the following optional conversions:

(i) when a compound of formula (I) is formed, converting it into a pharmaceutically acceptable derivative thereof;

(ii) when a pharmaceutically acceptable derivative of a compound of formula (I) is formed, converting the said derivative into a compound of formula (I), or a different derivative thereof;

(iii) converting the resulting compound of formula (I)) or a pharmaceutically acceptable derivative thereof into a different compound of formula (I) or pharmaceutically acceptable derivative thereof (e.g. substituting groups $R^1$ (in formula (A) above) or $R^2$ and/or $R^3$ (in formula (B) above) with a different such $R^1$, $R^2$ and/or $R^3$ group.

In the above-described process according to the invention, it will be appreciated that the precursor compounds of formula (II) as well as the above-mentioned agents and conditions, will be selected from those that are known in the art of nucleoside synthetic chemistry. Examples of such conversion procedures as described hereinafter for guidance and it will be understood that they can be modified in conventional manner depending on the desired compound of formula (I). In particular, where a conversion is described which would otherwise result in the undesired reaction of labile groups then such groups may be protected in conventional manner, with subsequent removal of the protecting groups after completion of the conversion.

With regard to process (A), $R_1$ may represent a protected hydroxy group e.g. an ester grouping particularly acetoxy or methoxycarbonyl, or an ether group such as a trialkylsilyloxy group, e.g. t-butyldimethylsilyloxy or an aralkoxy group e.g. triphenylmethoxy. Such groups may be converted for example by hydrolysis to the desired hydroxy group or, by transesterification, to an alternative ester group. $R_2$ may represent a group that is convertible on the introduction of an appropriate agent to the desired fluoro group to give the desired compound.

With regard to process (B), this may be effected for example by treating an appropriate purine or pyrimidine base of formula (III) or a salt or protected derivative thereof, with a 2',3'-dideoxythymidine for example in the presence of the appropriate pentosyl transferring enzyme, for example in the case wherein B is a purine base, using purine nucleoside phosphorylase and thymidine phosphorylase.

The compound of formula (I) wherein B represents uracil may be prepared as described for example by G. Kowollik et al. J. Prakt. Chem 1973, 315(5), 895–900.

The compounds of formula (I) in which the 5-position of the pyrimidine base is substituted with chlorine or iodine atom may be prepared for example by halogenating a corresponding compound of formula (I) in which B represents the desired unsubstituted base and in which the 5'-hydroxy group is blocked, for example by an acyl group such a p-tolyoyl group. Halogenation of the above starting material may be effected in conventional manner, for example iodination using iodine monochloride, e.g. in methylene dichloride, bromination using bromine e.g. in glacial acetic acid, and chlorination using a chlorine complex of iodobenzene, e.g. in glacial acetic acid.

The above tolyoyl derivative may be prepared by treating the appropriate compound of formula (I) with for example p-toluoyl chloride, eg in pyridine. After halogenation as described above, the p-toluoyl protecting group may be removed for example by sodium methoxide in methanol.

A compound of formula (I) may be converted into a pharmaceutically acceptable ester by reaction with an appropriate esterifying agent, e.g. an acid halide or anhydride. The compound of formula (I), including esters thereof, may be converted into pharmaceutically acceptable salts thereof in conventional manner, e.g. by treatment with an appropriate base. An ester or salt of a compound of formula (I) may be converted into the parent compound, e.g. by hydrolysis.

The following Examples are intended for illustration only and are not intended to limit the scope of the invention in any way. The term 'active ingredient' as used in the Examples means a compound of formula (I) or a pharmaceutically acceptable derivative thereof.

EXAMPLE 1: Tablet Formulations

The following formulations A and B are prepared by wet granulation of the ingredients with a solution of povidone, followed by addition of magnesium stearate and compression.

| Formulation A | | mg/tablet | mg/tablet |
|---|---|---|---|
| (a) | Active ingredient | 250 | 250 |
| (b) | Lactose B.P. | 210 | 26 |
| (c) | Providone B.P. | 15 | 9 |
| (d) | Sodium Starch Glycollate | 20 | 12 |
| (e) | Magnesium Stearate | 5 | 3 |
| | | 500 | 300 |

| Formulation B | | mg/tablet | mg/tablet |
|---|---|---|---|
| (a) | Active ingredient | 250 | 250 |
| (b) | Lactose | 150 | — |
| (c) | Avicel PH 101 | 60 | 26 |
| (d) | Providone B.P. | 15 | 9 |
| (e) | Sodium Starch Glycollate | 20 | 12 |
| (f) | Magnesium Stearate | 5 | 3 |
| | | 500 | 300 |

| Formulation C | mg/tablet |
|---|---|
| Active ingredient | 100 |
| Lactose | 200 |
| Starch | 50 |
| Povidone | 5 |
| Magnesium stearate | 4 |
| | 359 |

The following formulations, D and E, are prepared by direct compression of the admixed ingredients. The lactose used in formulation E is of the direct compression type (Dairy Crest - "Zeparox").

| Formlulation D | mg/capsule |
|---|---|
| Active ingredient | 250 |
| Pregelantinised Starch NF15 | 150 |
| | 400 |

| Formulation E | mg/capsule |
|---|---|
| Active ingredient | 250 |
| Lactose | 150 |
| Avicel | 100 |
| | 500 |

Formulation F (Controlled Release Formulation)

The formulation is prepared by wet granulation of the ingredients (below) with a solution of povidone followed by the addition of magnesium stearate and compression.

| | | mg/tablet |
|---|---|---|
| (a) | Active ingredient | 500 |
| (b) | Hydroxypropylmethylcellulose (Methocel K4M Premuim) | 112 |
| (c) | Lactose B.P. | 53 |
| (d) | Povidone B.P.C. | 28 |
| (e) | Magnesium Stearate | 7 |
| | | 700 |

Drug release takes place over a period of about 6–8 hours and is complete after 12 hours.

EXAMPLE 2: Capsule Formulations

Formulation A

A capsule formulation is prepared by admixing the ingredients of Formulation D in Example 1 above and filling into a two-part hard gelatin capsule. Formulation B (infra) is prepared in a similar manner.

| Formulation B | | mg/capsule |
|---|---|---|
| (a) | Active ingredient | 250 |
| (b) | Lactose B.P. | 143 |
| (c) | Sodium Starch Glycollate | 25 |
| (d) | Magnesium Stearate | 2 |
| | | 420 |

| Formulation C | | mg/capsule |
|---|---|---|
| (a) | Active ingredient | 250 |
| (b) | Macrogol 4000 BP | 350 |
| | | 600 |

Capsules are prepared by melting the Macrogol 4000 BP, dispersing the active ingredient in the melt and filling the melt into a two-part hard gelatin capsule.

| Formulation D | mg/capsule |
|---|---|
| Active ingredient | 250 |
| Lecithin | 100 |
| Arachis Oil | 100 |
| | 450 |

Capsules are prepared by dispersing the active ingredient in the lecithin and arachis oil and filling the dispersion into soft, elastic gelatin capsules.

| Formulation E (Controlled Release Capsule) The following controlled release capsule formulation is prepared by extruding ingredients a, b and c using an extruder, followed by spheronisation of the extrudate and drying. The dried pellets are then coated with release- controlling membrane (d) and filled into a two-piece, hard gelatin capsule. | | |
|---|---|---|
| | | mg/capsule |
| (a) | Active Ingredient | 250 |
| (b) | Microcrystalline Cellulose | 125 |
| (c) | Lactose BP | 125 |
| (d) | Ethyl Cellulose | 13 |
| | | 513 |

EXAMPLES 3: Injectable Formulation

| Formulation A | |
|---|---|
| Active ingredient | 0.200 g |
| Hydrochloric acid solution, 0.1M | q.s. to pH 4.0 to 7.0 |
| Sodium hydroxide solution, 0.1M | q.s. to pH 4.0 to 7.0 |
| Sterile water | q.s. to 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

| Formulation B | |
|---|---|
| Active ingredient | 0.125 g |
| Sterile, pyrogen-free, pH 7 phosphate buffer, | q.s. to 25 ml |

EXAMPLE 4: Intramuscular Injection

| Active Ingredient | | 0.20 g |
|---|---|---|
| Benzyl Alcohol | | 0.10 g |
| Glycofurol 75 | | 1.45 g |
| Water for Injection | q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE 5: Syrup

| Active ingredient | | 0.25 g |
|---|---|---|
| Sorbitol Solution | | 1.50 g |
| Glycerol | | 2.00 g |
| Sodium Benzoate | | 0.005 g |
| Flavour, Peach 17.42.3169 | | 0.0125 ml |
| Purified Water | q.s. to | 5.00 ml |

The active ingredient is dissolved in a mixture of the glycerol and most of the purified water. An aqueous solution of the sodium benzoate is then added to the solution, followed by addition of the sorbitol solution and finally the flavour. The volume is made up with purified water and mixed wall.

EXAMPLE 6: Suppository

| | mg/suppository |
|---|---|
| Active Ingredient (63 μm)* | 250 |
| Hard Fat, BP (Witapsol H15 - Dynamit NoBel) | 1770 |
| | 2020 |

*The active ingredient is used as a powder wherein at least 90% of the particles were of 63 μm diameter or less.

One-fifth of the Witepsol H15 is melted in a steam-jacketed pan at 45° C. maximum. The active ingredient is sifted through a 200 μm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 lm stainless steel screen and, with continuous stirring, is allowed to cool to 40° C. As a temperature of 38° C. to 40° C., 2.02 g of the mixture is filled into suitable, 2 ml plastic moulds. The suppositories are allowed to cool to room temperature.

EXAMPLE 7: Pessaries

| | mg/pessary |
|---|---|
| Active ingredient (63 μm) | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture.

EXAMPLE 8

5-Iodo-1-(2,3-dideoxy-3-fluoro-β-D-erythro-pentofuranosyl)uracil p-Toluoyl chloride (freshly distilled, 325 mg, 2.10 mmol) was added to a solution of 1-(2,3-dideoxy-3-fluoro-β-D-erythro-pentofuranosyl)uracil (440 mg, 1.91 mmol) in dry pyridine (10 ml). The solution was stirred at 50° C. for 1.5 hour, and then at 25° for 18 hours. The pyridine was evaporated and the residue dissolved in $CHCl_3$ (25 ml). This solution was extracted with 1M $H_2SO_4$ (5 ml), then $H_2O$ (2×10 ml), and dried ($MgSO_4$). Evaporation of $CHCl_3$ left a colourless glass (0.72 g) which was chromatographed on silica gel. Elution with 2% MeOH-CHCl₃ gave the 5'-O-toluoyl derivative as white solid foam (0.66 g, 90%); chromatographically homogeneous on TLC plates (silica gel developed with 5% MeOH-CHCl₃); structure confirmed by $^1$H-NMR.

The 5'-O-toluoyl derivative of 1-(2,3-dideoxy-3-fluoro-β-D-erythropentofuranosyl)uracil (200 mg, 0.574 mmol), iodine monochloride (139 mg, 0.861 mequiv), and $CH_2Cl_2$ (10 ml) were refluxed for 2 hours. The solution was decolourised with a minimum of 2% aqueous $NaHSO_3$ (ca. 2 ml). The aqueous layer was separated and the $CH_2Cl_2$ layer washed with $H_2O$ (2×5 ml) and dried ($MgSO_4$). Evaporation of $CH_2Cl_2$ left a cream colored solid foam (0.25 g) which was dissolved in MeOH (10 ml) and stirred with sodium methoxide (0.57 mmol) under $N_2$ at 25° for 18 hours. The solution was neutralized with Dowex 50W-X8 ($H^+$ form) resin. The resin was filtered off, washed with MeOH, and the contents of the methanol filtrate wash chromatographed on silica gel. Elution with 10% MeOH-$CH_2Cl_2$ gave a product as a white solid (0.135 g). Recrystallization from EtOH gave title compound as white crystals (115 mg, 55% overall yield); m.p. 197.5°–198° dec;

Anal: Calcd for $C_9H_{10}FIN_2O_4$: C, 30.36; H, 2.83; N, 7.87; F, 5.34; I, 35.64. Found: C, 30.50; H, 2.85; N, 7.85; F, 5.31; I, 35.51; UV max ($H_2O$): 286 nM; structure further confirmed by $^1$H-NMR and mass spectrum.

EXAMPLE 9

5-Chloro-1-(2,3-dideoxy-3-fluoro-β-D-erythro-pentofuranosyl)uracil

The chlorine complex of iodobenzene was freshly prepared as described in the literature (see M. J. Robins, et al., *Can. J. Chem.* 1982, 60, 554) and 246 mg (0.895 mmol) added to a solution of the 5'-O-toluoyl derivative of 1-(2,3-dideoxy-3-fluoro-β-D-erythro-pentofuranosyl) uracil (260 mg, 0.746 mmol), prepared as described in Example 8, in glacial acetic acid (4 ml). This solution was maintained at 80° under nitrogen for 20 minutes and evaporated to a white solid foam. Treatment with sodium methoxide in methanol was carried out as in Example 1. Chromatography on 2 mm thick silica gel plates (20×20 cm) developed in CHCl₃: MeOH: NH₄OH/180:20:1 was required to separate 5-chlorouracil (slightly greater $R_f$) from title compound, isolated as an off-white solid (46 mg). Trituration in methanol gave title compound as white needles (34 mg); m.p. 183°–184° C.;

Anal. Calcd for $C_9H_{10}ClFN_2O_4$: C, 40.85; H, 3.81; Cl, 13.40; N, 10.59. Found: C, 40.71; H, 5.85; Cl, 13.31; N, 10.55; UV λ max ($H_2O$) 275 nm; structure further confirmed by $^1$H-NMR and mass spectrum.

EXAMPLE 10

6-Cyclopropylamino-9-(β-D-2',3'-dideoxy-3'-fluororibofuranosyl)-9H-purine

6-Cyclopropylaminopurine (2.2 mmoles, 0.42 g) and 2',3'-dideoxy-3'-fluorothymidine (1.1 mmoles, 0.29 g) were dissolved in 10 ml N'N'-dimethylformamide and further diluted with 35 ml of a 10 mM potassium phosphate buffer with a pH of 6.8 and containing 0.04% potassium azide. Purified thymidine phosphorylase (5,000 I.U.) and purine nucleoside phosphorylase (10,000 I.U.) (Krenitsky, et al., *Biochemistry,* 20, 3615, 1981 and U.S. Pat. No. 4,381,444) adsorbed onto 5 ml of DEAE resin were added and the suspension was stirred at 35° C. On the twelth day, an additional 5,000 I.U. of purified thymidine phosphorylase and 10,000 I.U. of purine nucleoside phosphorylase adsorbed onto 5 ml of DEAE resin were added to the reaction mixture. On the thirteenth day the reaction was filtered and the filtrate was applied to a series of coupled columns. The initial 2.5×10 cm contained Dowex-1-hydroxide while the second 2.5×20 cm column was filled with Amberlit XAD-2 resin. After sample application, the columns were washed with a large volume of water and the product was eluted with methanol. Approximately 5 ml of dry silica gel were added to the product containing fractions and the solvent was evaporated under vacuum. This silica gel was applied to a 2.5×50 cm column of silica gel and the product was eluted with a 9:1/CHCl₃:MeOH mixture. Product containing fractions were combined and the solvent was removed under vacuum. The solid material was dissolved in 10 ml of 95% EtOH. After removal of the solvent under vacuum, the product was again dissolved in 10 ml of 95% EtOH and filtered to remove the remaining traces of silica gel. The solvent was removed under vacuum, the product was dissolved in water, and lyophilization yielded 0.084 g of 6-cyclopropylaminopurine-9-(β-D-2', 3'-dideoxy-3'-fluororibofuranosyl)-9H-purine.

Anal. Calcd. for $C_{13}H_{16}FN_5O_2$:C,53.24; H, 5.50; N, 23.88; F, 6.48; Found: C,53.42; H, 5.56; N, 23.73; F, 6.26.

EXAMPLE 11

2-Amino-6-methoxy-9-(β-D-2',3'-dideoxy-3'-fluororibofuranosyl)-9H-purine

2-Amino-6-methoxypurine was prepared by nucleophilic displacement of the chlorine group on 2-amino-6-chloropurine by sodium methoxide.

2-Amino-6-methoxypurine (3.1 mmoles, 0.51 g) and 2',3'-dideoxy-3'-fluorothymidine (1.3 mmoles 0.35 g) were dissolved in 5 ml N'N'-dimethylformamide and 5 ml dimethylsulfoxide. The reaction was further diluted with 30 ml of 10 mM potassium phosphate buffer, pH of 6.8, containing 0.04% potassium azide. Purified thymidine phosphorylase (3,300 I.U.) and purine nucleoside phosphorylase (6,900 I.U.) (Krenitsky, et al., *Biochemistry,* 20, 3615, 1981 and U.S. Pat. No. 4,381,444) adsorbed onto 3 ml of DEAE resin were added and the suspension was stirred at 35° C. After 6 days, an additional 3,300 I.U. of purified thymidine phosphorylase and 6,900 I.U. of purine nucleoside phosphorylase adsorbed onto 5 ml of DEAE resin were added to the reaction mixture. After another 7 days, 3,300 I.U. of purified thymidine phosphorylase and 6,900 I.U. of purine nucleoside phosphorylase adsorbed onto 5 ml DEAE resin were added to the reaction mixture. After an additional 23 days, for a total of 36 days of reaction, the reaction was filtered and the filtrate was applied to a series of coupled columns. The initial 2.5×10 cm column contained Dowex-1-hydroxide while the second 2.5×20 cm column was filled with Amberlite XAD-2 resin. After sample application, the columns were washed with a large volume of water and the product was eluted with methanol. Approximately 5 ml of dry silica gel were added to the product containing fractions and the solvent was evaporated under vacuum. This silica gel was applied to a 2.5×50 cm column of silica gel and the product was eluted with a 9:1/CHCl₃:MeOH mixture. Product containing fractions were combined and the solvent was removed under vacuum. The solid material was dissolved in 10 ml of 95% EtOH. After removal of the solvent under vacuum, the product was again dissolved in 10 ml of 95% EtOH and filtered to remove remaining traces of silica gel. The solvent was removed under vacuum, the product was dissolved in water, and lyophilization yielded 0.204 g of 2-amino-6-methoxypurine-9-(β-D-2',3'-dideoxy-3'-fluororibofuranosyl)-9H-purine.

Anal. Calcd. for $C_{13}H_{16}FN_5O_2$: C, 46.64; H, 4.98; N, 24.72; F, 6.71; Found: C, 46.10; H, 5.09; N, 23.96; F, 6.74.

$^1$H NMR and mass spectral data are consistent with the structure.

EXAMPLE 12

6-Cyclopentoxy-9-(β-D-2,3-dideoxy-3-fluororibofuranosyl)-9H-purine

6-Cyclopentoxypurine was prepared by nucleophilic displacement of the chlorine group on 6-chloropurine (Sigma Chemical Company, St. Louis, Mo.) by the alkoxy anion formed between sodium hydride and cyclopentanol.

6-Cyclopentoxypurine (4.9 mmoles, 1 g) and 2',3'-dideoxy-3'-fluorothymidine (2.1 mmoles, 0.50 g) were suspended in 5 ml N',N'-dimethylformamide and 5 ml methyl sulfoxide and further diluted with 35 ml of 10 mM potassium phosphate buffer, pH of 6.8, containing 0.04% potassium azide. Purified thymidine phosphorylase (5,000 I.U.) and purine nucleoside phosphorylase (10,000 I.U.) (Krenitsky, et al., *Biochemistry*, 20, 3615, 1981 and U.S. Pat. No. 4,381,444) adsorbed onto 5 ml of DEAE resin were added and the suspension was stirred at 34° C. After 35 days, an additional 3,000 I.U. of purified thymidine phosphorylase and 6,000 I.U. of purine nucleoside phosphorylase adsorbed onto 3 ml of DEAE resin were added to the reaction mixture. After an additional 21 days, the reaction was filtered and the filtrate was applied to a series of coupled columns. The initial 2.5×10 cm column contained AG1-X2 (OH- form) while the second 2.5×20 cm column was filled with Amberlite XAD-2 resin. After sample application, the columns were washed with a larger volume of water and the product was eluted with methanol. The product was then flash chromatographed on a silica gel column (2.5×48 cm) with dicloromethane:methanol (9:1). Solvent was removed under vacuum, the product was dissolved in water, and lyophilization yielded 0.162 g of 6-cyclopentoxy-9-(β-D-2,3-dideoxy-3-fluororibofuranosyl)-9H-purine.

Anal. Calcd. for $C_{15}H_{19}FN_4O_3$: C,55.89; H,5.94; N,17.38; Found: C,56.01; H,5.94; N,17.20.

Mass spectral and NMR data were consistent with the structure.

EXAMPLE 13

6-Isopropoxy-9-(β-D-2,3-dideoxy-3-fluororibofuranosyl)-9H-purine

6-Isopropoxypurine (5.0 mmoles, 0.90 g) (Sigma Chemical Company, St. Louis, Mo.) and 2',3'-dideoxy-3'-fluorothymidine (2.0 mmoles, 0.50 g) were suspended in 5 ml N',N'-dimethylformamide and 5 ml methyl sulfoxide and further diluted with 35 ml of 10 mM potassium phosphate buffer, pH of 6.8, containing 0.04% potassium azide. Purified thymidine phosphorylase (5,000 I.U.) and purine nucleoside phosphorylase (10,000 I.U.) (Kranitsky, et al., *Biochemistry*, 20, 3615, 1981 and U.S. Pat. No. 4,381,444) adsorbed onto 5 ml of DEAE resin were added and the suspension was stirred at 34° C. After 35 days, an additional 3,000 I.U. of purified thymidine phosphorylase and 6,000 I.U. of purine nucleoside phosphorylase adsorbed onto 3 ml of DEAE resin were added to the reaction mixture. After an additional 28 days, the reaction was filtered and the filtrate was applied to a series of coupled columns. The initial 2.5×10 cm column contained AG1-X2 (OH- form) while the second 2.5×20 cm column was filled with Amberlite XAD-2 resin. After sample application, the columns were washed with a large volume of water and the product was eluted with methanol. The product was then flash chromatographed on a silica gel column (2.5×48 cm) with dichloromethane:methanol (9:1). The product was dissolved in 25% acetonitrile and applied to a $C_{18}$ HPLC column (Microsorb 22 mm [ID] ×500 mm) and eluted with 25% acetonitrile at 18 ml/min. Solvent was removed under vacuum, the product was dissolved in water, and lyophilization yielded 0.240 g 6-isopropoxy-9-(β-D-2,3-dideoxy-3-fluororibofuranosyl)-9H-purine that analyzed as a 0.15 hydrate.

Analysis for $C_{13}H_{17}FN_4O_3 \cdot .015\ H_2O$: Calcd.: C,52.70; H,5.78; N,18.91; F,6.41; Found: C,52.46; H,5.78; N,18.48; F,6.49.

Mass spectral and NMR data were consistent with the structure.

EXAMPLE 14

6-Piperidinyl-9-(β-D-2,3-dideoxy-3-fluororibofuranosyl)-9H-purine

6-Piperidinylpurine (5.1 mmoles, 1.0 g) (Sigma Chemical Company, St. Louis, Mo.) and 2',3'-dideoxy-3'-fluorothymidine (2.0 mmoles, 0.50 g) were suspended in 5 ml N',N'-dimethylformamide and 5 ml methyl sulfoxide and further diluted with 35 ml of 10 mM potassium phosphate buffer, pH of 6.8, containing 0.04% potassium azide. Purified thymidine phosphorylase (5,000 I.U.) and purine nucleoside phosphorylase (10,000 I.U.)(Krenitsky, et al., *Biochemistry*, 20, 3615, 1981 and U.S. Pat. No. 4,381,444) adsorbed onto 5 ml of DEAE resin were added and the suspension was stirred at 34° C. After 35 days, an additional 3,000 I.U. of purified thymidine phosphorylase and 6,000 I.U. of purine nucleoside phosphorylase adsorbed onto 3 ml of DEAE resin were added to the reaction mixture. After an additional 58 days, the reaction was filtered and the filtrate was applied to a series of coupled columns. The initial 2.5×10 cm column contained AG1-X2 (OH- form) while the second 2.5×20 cm column was filled with Amberlite XAD-2 resin. After sample application, the columns were washed with a large volume of water and the product was eluted with methanol. The product was then flash chromatographed on a silica gel column (5×20 cm) with dichloromethane:methanol (9:1). Solvent was removed under vacuum, the product was dissolved in water, and lyophilization yielded 0.197 g 6-piperidinyl-9-(β-D-2,3-dideoxy-3-fluororibofuranosyl)-9H-purine that contained 0.35 ethanol.

Analysis for $C_{15}H_{20}FN_5O_2 \cdot 0.15$ EtOH: Calcd.: C,55.88; H,6.60; N,20.75; F,5.63; Found: C,55.72; H,6.48; N,20.80; F,5.78.

Mass spectral and NMR data were consistent with the structure.

Antiviral Activity

The anti-HIV activity of the compounds of Examples 8, 9 and 11 was assayed in MT4 cells and $IC_{50}$ values of 1.5, 12.4 and 9.0 μM respectively were obtained.

We claim:

1. A method of treating an HIV infection in a human having an HIV infection which comprises orally administering to said human in a capsule or tablet unit dose, 1 to 15 mg per kilogram human body weight per day of the compound 5-chloro-1-(2,3-dideoxy-3-fluoro-β-D-erythro-pentofuranosyl)uracil, said compound being given to said human 2 to 6 times per day and each capsule or tablet containing 10 to 1500 mg of the compound.

2. A method of treating an HIV infection in a human having an HIV infection which comprises administering to said human 1 to 15 mg per kilogram human bodyweight per day of the compound 5-chloro-1-(2,3-dideoxy-3-fluoro-β-D-erythropentofuranosyl)uracil.

3. A method according to claim 2 in which the compound is administered two to six times per day in sub doses.

4. A method according to claim 3 in which each sub dose contains 50 to 700 mg of the compound.

5. The method of claim 2 in which the compound is administered orally.

6. The method of claim 3 in which the compound is administered orally.

7. A method of treating an HIV infection in a human which comprises administering to said human an effective HIV treatment amount of the compound 5-chloro-1-(2,3-dideoxy-3-fluoro-β-D-erythro-pentofuranosyl)uracil in a tablet or capsule formulation.

8. A method of treating an HIV infection in a human which comprises injecting a liquid formulation containing an effective HIV treatment amount of the compound 5-chloro-1-(2,3-dideoxy-3-fluoro-β-D-erythro-pentofuranosyl)uracil into said human.

* * * * *